United States Patent
Björklund et al.

(10) Patent No.: US 6,706,488 B2
(45) Date of Patent: Mar. 16, 2004

(54) APOPTOSIS-RELATED COMPOUNDS AND THEIR USE

(75) Inventors: Viveka Björklund, Bromma (SE); Bertil Björklund, Bromma (SE); Peter Björklund, Bromma (SE); Marius Nap, Berg en Terblijt (NL); Frans C. S. Ramaekers, Maastricht (NL); Bert Schutte, Eÿsden (NL)

(73) Assignee: Peviva AB, Bromma (SE)

( * ) Notice: Subject to any disclaimer, the term of this patent is extended or adjusted under 35 U.S.C. 154(b) by 31 days.

(21) Appl. No.: 09/915,374

(22) Filed: Jul. 27, 2001

(65) Prior Publication Data

US 2002/0197657 A1 Dec. 26, 2002

Related U.S. Application Data

(62) Division of application No. 09/162,366, filed on Sep. 29, 1998, now Pat. No. 6,296,850.
(60) Provisional application No. 60/060,556, filed on Sep. 30, 1997.

(30) Foreign Application Priority Data

Sep. 30, 1997 (SE) ................................................ 9703546

(51) Int. Cl.$^7$ ...................... G01N 33/53; G01N 33/567; G01N 33/574; C07K 16/18
(52) U.S. Cl. ................................. 435/7.1; 435/4; 435/6; 435/7.2; 435/7.21; 435/7.23; 436/63; 530/387.1; 530/387.9; 530/388.1; 530/389.1; 530/391.1
(58) Field of Search ...................... 435/4, 6, 7.1, 7.2, 435/7.21, 7.23; 530/387.1, 387.9, 388.1, 389.1, 391.1

(56) References Cited

U.S. PATENT DOCUMENTS

5,660,994 A    8/1997   Bruder-Heid et al.

FOREIGN PATENT DOCUMENTS

WO             92/05197 A1    4/1992

OTHER PUBLICATIONS

Lane, E.B. et al., Cancer Biology, 1: 165–179, 1990.*
Giovagnoli, M.R. et al, Anticancer Res. 14: 635–642, 1994.*
Bantel, Eur. J. Cell Biology, 80: 230–239, 2001.*
Rydlander, L., et al. (1996) Eur. J. Biochem. 241: 309–314.*
Liao, J., et al., J. Cell Biol. 131:1291–1301, 1995.
Greidinger, E.L. et al., Sequential Activation of three distinct ICE–like activities in Fas–ligated Jurkat cells; FEBS Letters 390:299–303 (1996).
Guenal, I., et al., Down–regulation of actin genes precedes microfilament network disruption and actin cleavage during p53–mediated apoptosis; J. Cell Science 110:489–495. (1997).
Omary, M.B. et al., Keratin Modifications and Solubility Properties in Epithelial Cells and in Vitro; Subcelluar Biochemistry, 31: Intermediate Filaments, Eds. Herrmann and Harris, Plenum Press, New York, (1998) pp. 105–140.
Caulin et al., Journal of Cell Biology, 138:1379–1394 (1997).
Leube, R.E., et al.; Cytokeratim expression in simple epithelia. Differentiation, 3:69–85. (1986).
Oshima, R.G., et al.; Comparison of mouse and human keratin 18:A component of intermediate filaments expressed prior to implantation. Differentiation, 3:61–68. (1986).
Romano, V, et al.; Cytokeratin expression in simple epithelia. Differentiation, 30:244–253. (1986).
Sambrook, J. et al.; Molecular Cloning, A Laboratory Manual; 2nd Ed., Cold Spring Harbor Laboratory Press, pp. 18.26–18.29. (1989).

* cited by examiner

Primary Examiner—Anthony C. Caputa
Assistant Examiner—Anne L. Holleran
(74) Attorney, Agent, or Firm—Bacon & Thomas

(57) ABSTRACT

Apoptosis-related antigenic compounds comprising an exposed antigenic site having the amino acid sequence

```
SEQ ID NO: 1:
Glu Asp Phe Asn Leu Gly Asp Ala Leu Asp
1               5                   10
``` or a functionally equivalent sequence comprising at least the sequence Ala Leu Asp are disclosed. Further, several applications and uses based on such compounds are included, such as use of the compounds in medicaments, nucleic acid sequences encoding the amino-acid sequence of such a peptide compound or protein fragment comprising the C-terminal amino acid sequence Ala Leu Asp, anti-sense nucleic acid sequence, vector comprising such a nucleic acid sequence, antibody or antigen-binding peptide recognizing such an antigenic compound and use thereof in a medicament, agents regulating the liberation of protein fragments comprising the amino-acid sequence SEQ ID NO: 1 or functionally equivalent sequences comprising the C-terminal amino acid sequence Ala Leu Asp, a method of determining the occurrence of cell apoptosis in a sample of biological material, especially in the diagnosis of degenerative diseases and cancer, or monitoring of the effect of therapy, a method of treating diseases with involvement of apoptosis, such as cancer and degenerative diseases, a method of creating cancer cells, and as carrier for prophylactic, therapeutic or diagnostic use.

12 Claims, No Drawings

SEQUENCE LISTING

```
<160> NUMBER OF SEQ ID NOS: 22

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:  epitope
      from mammalian protein

<400> SEQUENCE: 1

Glu Asp Phe Asn Leu Gly Asp Ala Leu Asp
1               5                   10

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence:  epitope
      from mammalian protein

<400> SEQUENCE: 2

Glu Asp Gly Glu Asp Phe Asn Leu Gly Asp Ala Leu Asp Ser Ser Asn
1               5                   10                  15

Ser Met Gln Thr
            20

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence:  epitope
      from mammalian protein

<400> SEQUENCE: 3

Leu Glu Asp Gly Glu Asp Phe Asn Leu Gly Asp Ala Leu Asp Ser Ser
1               5                   10                  15

Asn Ser

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence:  epitope
```

```
                    from mammalian protein

<400> SEQUENCE: 4

Gly Glu Asp Phe Asn Leu Gly Asp Ala Leu Asp
  1               5                  10

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:   epitope
      from mammalian protein

<400> SEQUENCE: 5

Asp Ala Leu Asp
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:   epitope
      from mammalian protein

<400> SEQUENCE: 6

Leu Ala Leu Asp
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:   epitope
      from mammalian protein

<400> SEQUENCE: 7

Met Ala Leu Asp
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:   epitope
      from mammalian protein

<400> SEQUENCE: 8

Val Ala Leu Asp
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:   epitope
      from mammalian protein

<400> SEQUENCE: 9

Ser Gly Ser Gly
  1

<210> SEQ ID NO 10
```

```
<211> LENGTH: 13
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 10

Leu Glu Asp Gly Glu Asp Phe Asn Leu Gly Asp Ala Leu
 1               5                  10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 11

Leu Glu Asp Gly Glu Asp Phe Asn Leu Gly Asp Ala Leu Asp Ser
 1               5                  10                  15

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 12

Asp Gly Glu Asp Phe Asn Leu Gly Asp Ala Leu Asp
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 13

Glu Asp Gly Glu Asp Phe Asn Leu Gly Asp Ala Leu Asp
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 14

Gly Glu Asp Phe Asn Leu Gly Asp Ala Leu Asp
 1               5                  10

<210> SEQ ID NO 15
<211> LENGTH: 4
<212> TYPE: PRT
<213> ORGANISM: Artificial Sequence
<220> FEATURE:
<221> NAME/KEY: UNSURE
<222> LOCATION: (4)
<223> OTHER INFORMATION: x equals bAla
<223> OTHER INFORMATION: Description of Artificial Sequence: epitope
      from mammalian protein
```

```
<400> SEQUENCE: 15

Ser Gly Ser Xaa
  1

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 16

Asp Phe Asn Leu Gly Asp Ala Leu Asp
  1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 17

Phe Asn Leu Gly Asp Ala Leu Asp
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 18

Asn Leu Gly Asp Ala Leu Asp
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 19

Leu Gly Asp Ala Leu Asp
  1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: epitope
      from mammalian protein

<400> SEQUENCE: 20

Gly Asp Ala Leu Asp
  1               5

<210> SEQ ID NO 21
<211> LENGTH: 10
```

```
-continued

<212> TYPE: PRT
<213> ORGANISM: Artificial Sequence
<220> FEATURE:
<223> OTHER INFORMATION: Description of Artificial Sequence:  epitope
      from mammalian protein

<400> SEQUENCE: 21

Lys Arg Trp Gln Phe Gly Arg Leu Ala Arg
 1               5                  10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:  epitope
      from mammalian protein

<400> SEQUENCE: 22

Val Glu Val Asp Ala
 1               5
```

APOPTOSIS-RELATED COMPOUNDS AND THEIR USE

This application is a Division of nonprovisional application Ser. No. 09/162,366 filed Sep. 29, 1998 now U.S. Pat. No. 6,246,850, which claims the benefit of priority under 35 U.S.C. §119 of U.S. provisional application 60/060,556 filed on Sep. 30, 1997.

The present invention relates to apoptosis-related antigenic compounds, such as fragments of cytokeratin 18, and antibodies or antigen-binding peptides recognizing said compounds, which are useful in medicaments, diagnostics and methods for the detection, monitoring, measurement and regulation of the type of cell death called programmed cell death or apoptosis. The determination of the occurrence of cell apoptosis may further be used for the monitoring of the effect of therapeutic treatment.

BACKGROUND OF THE INVENTION

Apoptosis is seen in all sorts of higher eucaryocytes from plants and insects to vertebrates (Kroemer G, Petit P, Zanzami N, Vayssiere J -L, Mignotte B: The biochemistry of programmed cell death. The FASEB Journal 9:1277–1287 (1995)). Apoptosis is a general phenomenon of vital importance. Decreased apoptosis leads to malformation, cancer and autoimmune disease, and enhanced apoptosis results in degenerative diseases, acute diseases such as infection by toxin-producing microorganisms and in rejection of transplanted organs.

Therefore, the detection, monitoring, measurement and regulation of apoptosis are important factors in the diagnosis and therapeutic treatment of the mentioned conditions.

Recently, Caulin C., et al (The Journal of Cell Biology, Vol 138, pp. 1379–1394) studied caspase cleavage of Keratin 18 and reorganization of intermediate filaments during epitelial cell apoptosis. Keratin 18 was cleaved in vitro by caspase-6, -3, and -7, and it was stated that the cleavage site common for the three caspases was the sequence VEVD/A (SEQ ID NO:22), located in the conserved L1-2 linker region of K18.

DESCRIPTION OF THE INVENTION

During research work aiming at finding new useful specific monoclonal antibodies reacting with human cytokeratin 18 (CK 18), in addition to those already at hand, it was surprisingly found that a monoclonal antibody (MAb) (obtained after immunization of mice with a specified part of the amino-acid sequence of CK 18) recognized early apoptotic changes in cultured epithelial cells. This MAb was designated M30.

A detailed analysis, including synthesis and assay of a large number of amino-acid (aa) sequences revealed, that the specific epitope and binding-site for the MAb M30 consists of the aa sequence: EDFNLGDALD (SEQ ID NO:1). This 10 aa peptide sequence starts from the second coil of human CK 18 and represents aa No.383–392. This specific epitope is a neo-epitope liberated during apoptisis and it is not exposed in the intact CK 18 molecule. The complete aa sequence of CK 18 was published by Oshima et al. (Oshima R G, Millan J L, and Ceccena G. (1986). Comparison of mouse and human keratin 18: a component of intermediate filaments expressed prior to implantation. Differentiation 33:61–68.).

The different aspects of the present invention are based on the optimal binding site of the mAb M 30, i.e. the amino-acid sequence EDFNLGDALD,

```
SEQ ID NO: 1:
Glu Asp Phe Asn Leu Gly Asp Ala Leu Asp
1                   5                  10
```

Initially it was believed that an important part for apoptosis is related to cleavage by caspase enzymes immediately after DALD (Asp Ala Leu Asp) (SEQ ID NO:5), since this sequence occures in CK18 and caspases are known to cleave after DXXD wherein X stands for not defined aa.

However, the sequence DALD does not occur in such other intermediate filaments as CK 1–8, vimentin, desmin, different actins, neurofilaments, and lamins. In these the following sequences are found: LALD, MALD, MALD, VALD, MALD, and LALD (SEQ ID NOS:6, 7, 7, 8, 7 and 6), respectively.

Since the mAb M 30 recognizes apoptotic changes in non-epithelial cells such as cardiac muscle, megakaryocytes, myeloblasts and neural tissues of fetus—which are not known to contain CK18—it is now believed that detection of protein fragments having the C-terminal sequence ALD indicates early apoptosis.

Thus, one aspect of the invention is directed to an apoptosis-related antigenic compound which specifically binds to an antibody which in turn specifically binds to the amino-acid sequence

```
SEQ ID NO: 1:
Glu Asp Phe Asn Leu Gly Asp Ala Leu Asp
1                   5                  10,
``` i.e. an apoptosis-related antigenic compound comprising an exposed antigenic site having the amino acid sequence SEQ ID NO:1 or a functionally equivalent sequence. Further, the functionally equivalent sequence should comprise at least the sequence Ala Leu Asp.

It is the three-dimensional structure of the exposed antigenic site, or antibody-binding site, that defines the structure of the binding portion of an antigenic compound which specifically binds to the corresponding three-dimensional structure of an antibody. The antigenic compound of the invention therefore comprises compounds which are based on the structure of the SEQ ID NO:1, i.e. the sequence as such or a functionally equivalent sequence, i.e. homologous in function, comprising at least the sequence Ala Leu Asp, such as compounds having replacements of one or several amino acids in the above specified amino-acid sequence with other molecular parts, D- forms of the amino acids, non-natural amino acids and/or derivatives, as long as the three-dimensional structure of the SEQ ID NO:1 is mimicked. Therefore the common feature of the antigenic compounds of the invention is that they bind specifically to an antibody which in turn binds specifically to the aa sequence SEQ ID NO:1, i.e. antigenic compounds comprising an antigenic site having the amino acid sequence SEQ ID NO: 1 or a functionally equivalent sequence comprising at least the sequence Ala Leu Asp.

It can be mentioned that intact CK 18 molecules have the above-specified sequence hidden, and can therefore not react with antibodies specifically binding to said sequence, thereby making the recognition specific to apoptosis, i.e. those cases where the CK 18 molecule has been already cleaved after the C-terminal Asp of the sequence Asp Ala Leu Asp (SEQ ID NO:5).

In a preferred embodiment of this aspect of the invention, the apoptosis-related compound is a peptide or a protein fragment comprising the C-terminal amino acid sequence Ala Leu Asp. The peptide may be a homologue to, an extension of or a truncation of the SEQ ID NO: 1, i.e. may have a homologous sequence having some amino-acid substitutions, extensions, truncations and/or deletions which do not lead to the elimination of the capability of the peptide to bind to the same antibodies as the amino-acid sequence SEQ ID NO: 1.

In another preferred embodiment of this aspect of the invention the antigenic compound of the invention is a peptide or a protein fragment comprising the C-terminal amino acid sequence Xaa Ala Leu Asp, wherein Xaa is selected from Asp, Leu, Met, and Val (SEQ ID NOS:5, 6, 7 and 8).

An example of a peptide according to the invention is an oligopeptide having the amino-acid sequence

```
SEQ ID NO: 1:
Glu Asp Phe Asn Leu Gly Asp Ala Leu Asp
1               5                   10.
```

Another example is an oligopeptide having the amino-acid sequence (EDGEDFNLGDALDSSNSMQT)(i.e. SEQ ID NO: 1 extended by 3 amino acids at the N-terminal and 7 at the C-terminal)

```
SEQ ID NO: 2:
Glu Asp Gly Glu Asp Phe Asn Leu Gly Asp Ala Leu Asp Ser Ser Asn
1               5                   10                  15
Ser Met Gln Thr
            20.
```

Yet another example is an oligopeptide having the amino-acid sequence (LEDGEDFNLGDALDSSNS)

```
SEQ ID NO: 3:
Leu Glu Asp Gly Glu Asp Phe Asn Leu Gly Asp Ala Leu Asp Ser Ser
1               5                   10                  15
Asn Ser.
```

These peptides having the amino acid sequences SEQ ID NO: 2 and 3 have been synthesized, and in an ELISA they bind to the mAb M 30 [relative activity: 100 for SEQ ID NO: 1; 11 for SEQ ID NO: 2; and 8.3 for SEQ ID NO:3, respectively]. However, these two peptides are not expected to represent cleaved fragments of CK18 specific for apoptosis, since the mAb M 30 cannot bind to CK18 fragments until they expose the neo-epitope having the C-terminal sequence Ala Leu Asp.

Still another example is an oligopeptide having the amino-acid sequence (GEDFNLGDALD)

```
SEQ ID NO: 4:
Gly Glu Asp Phe Asn Leu Gly Asp Ala Leu Asp
1               5                   10
```

In the present specification and claims, specific binding of an antigenic compound to an antibody, or specific binding of an antibody to an amino-acid sequence, requires an affinity constant of at least $10^7$ liters/mole, preferably at least $10^9$ liters/mole.

In an embodiment of this aspect of the invention the antigenic compound is coupled to a carrier and/or label. The carrier may be e.g. plastic surfaces, such as microplates, beads etc.; organic molecules such as biotin; proteins, such as bovine serum albumin; peptide linkers, polypeptides e.g. resulting in fusion proteins.

The label may be selected from a variety of different types of labels, such as radioactive isotopes, enzymes, fluorescent markers, etc.

Another aspect of the invention is directed to an antigenic compound according to the invention for use in a medicament.

In a preferred embodiment of this aspect of the invention an antigenic compound according to the invention is used in the production of a medicament for inhibition of cell apoptosis.

Inhibition of cell apoptosis may be desirable in the treatment of degenerative conditions, such as anorexia, AIDS, transplantation of organs, psoriasis, and Alzheimer's disease.

Yet another aspect of the invention is directed to an isolated or recombinant nucleic acid sequence comprising a nucleotide sequence which encodes an amino-acid sequence of a peptide or protein fragment according to the invention.

A nucleic acid sequence of the present invention may be either in the form of RNA or DNA (including cDNA, genomic DNA and synthetic DNA). The DNA may be double-stranded or single-stranded. When the DNA sequence is single-stranded, it may be either the coding sequence (sense strand) or non-coding sequence (anti-sense strand). The nucleic acid sequences of the invention can be designed from the amino-acid sequence of a peptide or protein fragment comprised by the invention with the aid of the genetic code.

The nucleic acid sequences of the invention can be used in the production of proteins, polypeptides, oligopeptides and peptides of the invention. In a particular embodiment of this aspect of the invention, the nucleic acid sequence is an anti-sense sequence based on the nucleic acid sequence of the invention, which is complementary, in whole or at least a part of the SEQ ID NO: 1 encoding part, to a sense sequence encoding a peptide or a protein fragment of the invention. When introduced into a cell, the anti-sense nucleic acid sequence can inhibit the expression of the gene encoded by the sense strand.

This aspect of the invention also involves a vector comprising a nucleic acid sequence of the invention. Such a vector may be used in the production of a peptide or protein fragment of the invention or possibly in the regulation of the amount of protein fragments comprising the amino acid sequence SEQ ID NO: 1 or functional equivalents thereof comprising at least the sequence Ala Leu Asp in target cells, in vivo or in vitro. In a preferred embodiment of the invention, the vector is a plasmid.

Still another aspect of the invention is directed to an antibody or antigen-binding peptide recognizing an antigenic compound according to the invention.

The antibody of the invention may be a monoclonal antibody or monospecific polyclonal antibody recognizing or specifically binding to an antigenic compound according to the invention, i.e. recognizing or specifically binding to the amino-acid sequence SEQ ID NO: 1 or a functionally equivalent sequence comprising at least the sequence Ala Leu Asp. The antibody of the invention can be prepared by using immunization procedures well known in the art, or by well known methods based on recombinant technology making use of suitable host cells of eukaryotic or prokaryotic origin.

The antigen-binding peptide recognizing an antigenic compound according to the invention may be the antigen-binding part of an antibody, or a protein or peptide which has an amino-acid sequence that at least in the part corresponds to the amino-acid sequence SEQ ID NO: 1 or its functional equivalent comprising at least the sequence Ala Leu Asp but has amino acids with the opposite charges. Such an antigen-binding peptide will function as an antagonist.

In the development of antagonists the following guideline may be used:
o=hydrophobic amino acid
+=positive amino acid
−=negative amino acid
±=neutral amino acid

```
SEQ ID NO: 1:       E D F N L G D A L D
                    - - o ± o ± - o o -
corresponding site
of antagonist:      + + o ± o ± + o o +
                e.g.K R W Q F G R L A R
```

A number of antagonist candidates may be designed with the aid of the above guideline, especially variants where K and R are used for the + positions.

In an embodiment of this aspect of the invention the antibody or antigen-binding peptide is coupled to a carrier and/or label.

The carrier may be e.g. plastic surfaces, such as microplates, beads etc.; organic molecules such as biotin; proteins, such as bovine serum albumin; peptide linkers, polypeptides e.g. resulting in fusion proteins.

The label may be selected from a variety of different types of labels, such as radioactive isotopes, enzymes, fluorescent markers, etc.

A further aspect of the invention is directed to the antibody and antigen-binding peptide of the invention for use in a medicament.

In a preferred embodiment of this aspect of the invention an antibody or antigen-binding peptide of the invention is used in the production of a medicament for the stimulation of apoptosis, particularly in conditions such as malformation, cancer and autoimmune disease, i.e. conditions relating to uncontrolled or excessive cell proliferation.

In another embodiment of the invention the produced medicament is desirable in the treatment of diseases with involvement of enhanced apoptosis, such as many degenerative diseases, or acute diseases; such as infection by toxin-producing microorganisms or ischemic-reperfusion damage and rejection of transplanted tissue or organs. Here, medical control of apoptosis may be of utmost importance.

Yet another aspect of the invention is directed to agents regulating the liberation in biological material, including the mammalian body or cell culture, of protein fragments comprising the C-terminal amino-acid sequence Ala Leu Asp.

Examples of such agents of the invention are nucleic acid sequences of the invention, either inhibiting (sense strand) or stimulating (anti-sense strand), the expression of proteins comprising the sequence SEQ ID NO: 1 or sequences specifically binding to the same antibodies or antigen-binding peptides as the SEQ ID NO: 1, i.e. functionally equivalent sequences comprising at least the sequence Ala Leu Asp, and enzymes, enzyme activators and inhibitors.

Still another aspect of the invention is directed to a method of determining the occurrence of cell apoptosis in a biological sample including a sample of an organ, tissue or body fluid from a mammal, including man, wherein the presence of protein fragments comprising the C-terminal amino-acid sequence Ala Leu Asp, is determined.

In a preferred embodiment of this aspect of the invention the determination is performed with an immunological assay using the antibody of the invention.

In another preferred embodiment of this method the rate of occurrence of cell apoptosis is determined. The determined rate of cell apoptosis may be used in the diagnosis of diseases with involvement of apoptosis, such as degenerative diseases and cancer, and in the monitoring of the effect of therapy.

As origin of samples in this aspect the following may be mentioned: in vivo or in vitro, any organs, normal or changed, tissues, specimens and fluids of the human or animal body, for example liver, lung, kidney, heart, spleen, brain, viscera, lymphatic organs, bone-marrow, reproductive organs, skeleton, muscle, skin, sensory organs, glands, blood, serum, urine, ascitic fluid, pleural fluid, cerebrospinal fluid, amniotic fluid, abscess fluid, wash fluids, punctures, slices and any preparation of cellular or fluid origin in this context.

The determination of said protein fragments may be performed by any technique which can detect and preferably quantify the amount of peptide fragments comprising the C-terminal amino acid sequence Ala Leu Asp in a sample of body fluid. Preferably the protein fragments comprise at least the amino acid sequence SEQ ID NO: 1 or sequences specifically binding to the same antibodies or antigen-binding peptides as the SEQ ID NO: 1, i.e. functionally equivalent sequences comprising at least the sequence Ala Leu Asp. Monoclonal antibodies which specifically bind to said fragments can be used in different immunoassays, optionally labeled in accordance with the actual assay used.

In one embodiment of said method of the invention, the determination is performed with the aid of an immunoassay. Also, detection systems adapted for the use of antibody-site carrying structures and/or antibodies may be used. Some examples of the numerous immunoassays which may be used in the invention are Enzyme-linked immunosorbent assay (ELISA), Radioimmunoassay (RIA, IRMA), Fluorescence immunoassay (FIA), Chemiluminescent enzyme-labeled immunometric assay, Luminescence immunoassay (LIA), Dissociation enhancement time-resolved fluoroimmunoassay (DELFIA). The assay may be manual or automatic.

Further, an aspect of the invention is directed to a method of treating diseases with involvement of apoptosis, such as cancer and degenerative diseases, in a patient comprising administration of a cell apoptosis-regulating amount of an antibody or antigen-binding peptide according to the invention or of an antigenic compound according to the invention, to said patient.

Another aspect of the invention is directed to a method of creating cancer cells comprising administration of a cell apoptosis-inhibiting amount of an antigenic compound according to the invention to a cell culture or a laboratory animal. Such a cell culture or laboratory animal can be used in the production of desired polypeptides or proteins or in the evaluation of candidate anti-cancer drugs.

An additional aspect of the invention is directed to a carrier for prophylactic, therapeutic or diagnostic use comprising an antibody or antigen-binding peptide of the invention. Such a carrier of the invention will function as a targeting substance finding fragments comprising the C-terminal amino acid sequence Ala Leu Asp, such as SEQ ID NO: 1 or functionally equivalent sequences comprising at least the sequence Ala Leu Asp, and it may be coupled to a variety of medicaments and/or labels for prophylactic, therapeutic or diagnostic purposes.

The present invention will now be further illustrated by reference to the following description of experiments and specific embodiments of the invention, which are not to be considered as limitations to the scope of the invention defined in the claims.

Synthesis of Peptides of the Invention

The peptides of the invention can be produced by any known method of producing an amino-acid sequence, such as, controlled degradation of a purified protein by proteases or other chemical methods (Allen G., Sequencing of proteins and peptides, 1989, Elsevier Science Publishers B.V.). Chemical synthesis is commonly performed by coupling of the amino acid residues or peptide fragments to one another in correct order in liquid phase to produce the desired peptide. Another common strategy is the coupling of the amino acids to one another starting with a solid phase (resin) to which the C-terminal of the last amino acid of the sequence is coupled, whereupon the C-terminal of the penultimate amino acid is coupled to the N-terminal of the last amino acid, etc., finally releasing the built-up peptide from the solid phase (so called solid-phase technique).

The oligopeptides made in order to illustrate the invention were synthesized using the multipin peptide synthesis approach using polyethylene supports derivatized with an acid handle (Cf. Valerio, R. M. , Bray, A. M. and Maeji, N. J. (1994) Multiple peptide synthesis on acid-labile handle derivatized polyethylene supports. Int. J. Peptide Protein Res. 44:158–165.). The synthesis was carried out on detachable pins grafted with hydroxyethylmethacrylate and functionalized with the trifluoroacetic acid-labile Rink amide forming handle. Peptides representing both the N and C terminal truncation series of the sequence EDFNLGDALD (SEQ ID NO: 1) and other sequences were synthesized. Peptides were capped with biotin using the tetra peptide linker sequence -SGSG- or -SGSB- (B=β alanine), and attached to streptavidin coated plates in the enzyme-linked immunosorbent assay.

The aa sequences were checked for purity by reverse phase high performance liquid chromatography (RP-HPLC) and by ion spray mass spectrometry (IS-MS) (Cf. Van Dorsselear et al., (1990) Application of electrospray mass spectrometry to characterization of recombinant proteins up to 44 kDa. Biomed.Environ.Mass Spectrom. 19:692–704).

Ion spectra were collected as positive ions, obtained by vaporizing the peptide from acidic (trifluoroacetic or acetic acid) solution. Percentage of total ion count versus molecular weight (Dalton) was derived from the spectrum of raw mass-to-charge ratio versus ion count. The IS-MS purity value is the ion count, attributable to the target peptide, expressed as percentage of the total ion count.

Immunization of Mice

Preparation of Immunizing Material

The starting material for antigen purification consisted of the supernatant of cell culture medium from human colon carcinoma cell line WiDR (ATCC No. CCL 218) (Rydlander L, Ziegler E, Bergman T, Schöberl E, Steiner G, Bergman A-C, Zetterberg A, Marberger M, Björklund P, Skern T, Einarsson R and Jörnvall H (1996): Molecular characterization of a tissue-polypeptide-specific-antigen epitope and its relationship to human cytokeratin 18. Eur.J.Biochem. 241:309–314.) The first step utilized precipitation with 50% (mass/vol) ammonium sulfate. This was followed by hydrophobic-interaction chromatography on phenyl Sepharose in 14 mM phosphate/85 mM ammonium sulfate, pH 7.5. After washing of the column, hydrophobic proteins were eluted with water, and fractions collected. The third step consisted of Sephacryl S-300 exclusion chromatography in 8 M urea, 0.1 M Tris/HCl, pH 8.0. In the fourth step, Q Sepharose, equilibrated with 8 M urea in 0.1 M Tris/HCL, pH 8.0. was employed.

The fraction eluted at 0.12 M NaCl was about 882 times purified and contained two active components, one of 13 kD, another of 22 kD. They were identified as subtypes of cytokeratin 18, both ending at aa 396, i.e. fragments comprising a C-terminal aa sequence ALD.

Immunization Procedure

Four BalbC mice received one intraperitoneal (i.p.) injection of 100 μl of Freund's complete adjuvant suspended in 100 μl balanced salt solution (PBS) containing 107 μg of the first batch of the purified antigen. Three, six and nine weeks later, the mice received similar injections and amounts of an additional batch of the antigen, but with incomplete instead of complete Freund's adjuvant. Eight weeks after the last injection, a booster injection of 53 μg of a new batch of antigen without adjuvant in 100 μl PBS was given i.v. and the same amount was introduced i.p.

Immunization of BalbC mice with an appropriate dose of the synthesized peptide EDFNLGDALD (SEQ ID NO:1), coupled to the lipopeptide adjuvant: (Pam3cysSer(Lys)4, Boehringer 1428 764,lot 1312 7024), will result in development of immuno-competent cells producing monoclonal antibodies against the synthetic oligopeptide.

Hybridization

Three days after the booster injection of the mice, the spleen cells were hybridized with mouse myeloma cells (cell line: P3x63-Ag 8.653, G. Köhler)). Mediums from a large number of resulting hybridoma cultures were reacted with rabbit anti-mouse antibodies (solid phase), whereupon immunizing antigen and blocking mouse globulin were added, followed by HRP-labeled, detecting antibody against CK 18.

By immunocytochemical analyses it was observed that one of the resulting hybrid cell lines (No. 30) produced antibodies that reacted with cultured cells, that were neither vital nor necrotic. Among the cells tested were HeLa cells (Gey 1952), bladder carcinoma cell line T24, mammary cell line T47d, colon carcinoma cell line WiDr CCL 218 grown in IMDM 90%+10% fetal bovine serum+2 mm L-glutamine and 10 μg Gentamycine. The unexpected observations gave rise to detailed studies of the antibody specificity by immunochemical and immunocytochemical techniques. It became evident that the MAb, designated M30, reacted specifically with apoptotic cells and fluids.

Immunochemistry

In order to characterize the MAb M30-epitope chemically, the M30 was tested against a large number of synthetic peptides, that were especially made for this purpose. It was found that the optimal specific epitope consisted of the aa sequence EDFNLGDALD (SEQ ID NO:1). This and related sequences are presented in Table 1 which shows the reactivity of amino-acid sequences with the monoclonal antibody M 30 of the invention.

TABLE 1

| Peptide No. | Link to Biotin | Absorbance at 405/492 nm | Sequence |
|---|---|---|---|
| 63 | -SGSG- | 0.05 | LEDGEDFNLGDAL |
| 61 | -SGSG- | 0.1 | LEDGEDFNLGDALDS |
| 46 | -SGSG- | 0.77 | DGEDFNLGDALD |
| 45 | -SGSG- | 1.05 | EDGEDFNLGDALD |
| 47 | -SGSG- | 1.23 | GEDFNLGDALD |
| 302 | -SGSB- | 1.41 | GEDFNLGDALD |
| 301 | -SGSB- | 1.46 | EDFNLGDALD |
| 401 | -SGSB- | 0.62 | DFNLGDALD |
| 402 | -SGSB- | 0.27 | FNLGDALD |
| 403 | -SGSB- | 0.14 | NLGDALD |
| 404 | -SGSB- | 0.1 | LGDALD |
| 405 | -SGSB- | 0.1 | GDALD |
| 406 | -SGSB- | 0.1 | DALD |

Note. B = β alanine

As is evident from Table 1, gradual shortening of the sequence from the amino end to EDFNLGDALD, (SEQ ID NO:1) gave maximal activity. At the other end, removal of the last D (Asp) or addition of an S (Ser) to the last D resulted in complete loss of activity.

The need for the last D in DALD is clear-cut and should be seen in connection with what is known about structures required for apoptosis: Active caspase-3 enzyme recognizes an DXXD pattern in target substrates (Nicholson D W, Ali A, Thornberry N A, Vaillancourt J P, Ding C K, Gallant M, Gareau Y, Griffin P R, Labelle M, Lazebnik Y A, Munday N A, Raju S R, Smulson M E, Yamin T -T, Yu V L, Miller D K, et al. (1995). Identification and inhibition of the ICE/CED-3 protease necessary for mammalian apoptosis. Nature. 376:37–43.). In addition, both caspase-6 and caspase-7 are able to cleave substrates with a DXXD sequence (Talanian R V, Quinlan C, Trautz S, Hacket M C, Mankovich J A., Banach D, Ghayur T, Brady K D. Wong W W. (1997). Substrate specificities of caspase family proteases. J.Biol.Chem.272:9677–9682.). So far, the new sequence described here has not been known before to indicate apoptosis.

That proteases of the caspase subfamily are involved in mammalian apoptosis is supported by compelling evidence ranging from observation of DXXD-X cleaving activity and the activation of proenzymes in apoptotic cells, and the inhibition of apoptosis in a variety of systems by specific substrate-mimicking peptide inhibitors (Nobel S.(1997). Thiol redox state in apoptosis: Physiological and toxicant modulation. Dissertation, Karolinska Institutet, Stockholm, Sweden. ISBN 91-628-2502-X.).

Immunocytochemistry

Today there are several methods for the detection of apoptosis, but none is based on a defined reacting part of cytokeratin 18 with known amino acid sequence. The most widely used methods to identify apoptotic cells are light and electron microscopic analysis, flow cytometry, agarose gel electrophoresis, in situ nick-end labeling (ISEL) and the TdT-mediated dUTP Nick End Labeling (TUNEL)-technique.

To substantiate the preliminary findings, and to fit the expression of the epitope, recognized by the MAb M30, the effect of the different apoptosis systems were analyzed and a comparison made between M30-immunocytochemistry and accepted apoptosis assays. Comparisons were made using e.g. the non small cell lung cancer cell line MR65 with the annexin-, the TUNEL- and flow cytometric assays next to established morphological criteria. Confocal laser microscopic analysis revealed that apoptotic cells showed a bright immunofluorescence cytoplasmic staining after incubation with the MAb M30, while viable and necrotic cells turned out to be negative.

The expression of the M30-epitope correlated very well with other accepted staining methods for the detection of apoptotic cells i.e. annexin V-, TdT-mediated dUTP Nick End Labeling (TUNEL)-assay and morphological criteria. The majority of the M30-positive cells were in the "apoptotic" sub G1-peak. The expression of the M30-epitope occurred early in the apoptotic cascade, before annexin V reactivity or positive Nick end labeling. The epitope was not detectable in vital epithelial cells. The epitope, consisting of the aa sequence EDFNLGDALD (SEQ ID NO:1) or functionally equivalent sequences comprising at least the sequence Ala Leu Asp, allows quantification of apoptotic cells at the level of the cytoskeleton using simple immunocytochemical techniques.

The major drawbacks of the hitherto accepted methods for detection of apoptosis are that they are time consuming, relatively expensive, labor-intensive and not always specific for apoptotic cells. In addition, the TUNEL assay and the ISEL can only detect intermediate and late apoptosis.

When the effects of different apoptosis induction systems were analyzed and a comparison made between M30-immunocytochemistry and accepted apoptosis-assays, it turned out, that M30 is superior to existing apoptosis detection assays in cell lines and routinely obtained biopsies of human origin. M30 specifically recognizes apoptotic cells in the early stages of the process.

Since M30 recognizes the intrinsic early marker of apoptosis, i.e. EDFNLGDALD (SEQ ID NO:1) or functionally equivalent sequences comprising at least the sequence ALD, it is applicable to fresh and also formalin fixed, paraffin embedded tissue sections of routinely obtained biopsies. This is one of the advantages of M30.

Since M30-immunoreactivity also precedes both loss of membrane asymmetry, as is detected by annexin V-binding and DNA fragmentation, which is detected by the TUNEL assay, it offers distinctive advantages over presently used routine assays. Since apoptosis is implicated in many diseases, the specific, early detection and quantification of apoptotic cells is of utmost importance.

Body Fluids Reflecting Apoptosis

When apoptotic products containing EDFNLGDALD (SEQ ID NO:1), or functionally equivalent sequences comprising at least the sequence ALD, are released from apoptotic cellular areas in the body into body fluids such as serum, ascites, pleura, etc., immunoreactive assays can be used with MAb M30 just as with other serum assays to detect and quantify the concentration of special products in serum and body fluids. In this way one can differentiate between illnesses caused by or connected with enhanced or insufficient apoptosis i.e. increased or decreased levels of the MAb M30 binding site EDFNLGDALD (SEQ ID NO:1) or functionally equivalent sequences comprising at least the sequence ALD. Specimens from implicated organs or tissues can contribute to a more specific diagnosis.

Diagnostic Use of the SEQ ID NO: 1 or Functionally Equivalent Sequences

The process of apoptosis can be subdivided into three phases: the induction phase, the effector phase and the degradation phase. Cytokeratin 18 degradation and production of fragments containing EDFNLGDALD (SEQ ID NO:1) takes place very early and long before any of the known methods for assay of apoptosis turn positive. This makes it possible to interfere very early with the production and function of EDFNLGDALD (SEQ ID NO:1), or functionally equivalent sequences comprising at least the sequence ALD, with the aid of antagonistic medicals, specific antibodies to EDFNLGDALD (SEQ ID NO:1), or functionally equivalent sequences comprising at least the sequence ALD, and also inhibitors or activators of the enzymes that contribute to the production of EDFNLGDALD (SEQ ID NO:1) or functionally equivalent sequences comprising at least the sequence ALD.

By using the knowledge obtained from the analysis of concentration and localization of M30-positive specimens, it is possible to tell, if enhancement or inhibition of the process of apoptosis (programmed cell death) is desirable and if one should try to influence this process by labeled or unlabeled M30-antibody, more labeled or unlabeled EDFNLGDALD (SEQ ID NO:1), or functionally equivalent sequences comprising at least the sequence ALD, labeled or unlabeled antagonist to EDFNLGDALD (SEQ ID NO:1), functionally equivalent sequences comprising at least the sequence ALD, such as KRWQFGRLAR (SEQ ID NO:21) or similar, or by inhibiting or enhancing the enzyme producing EDFNLGDALD (SEQ ID NO:1) or functionally equivalent sequences comprising at least the sequence ALD. The choice is based upon the exact determination of the apoptotic amino acid sequence EDFNLGDALD (SEQ ID NO:1) or functionally equivalent sequences comprising at least the sequence ALD with the aid of the monoclonal antibody M30.

What is claimed is:

1. A method of determining the occurrence of cell apoptosis in a biological sample from a mammal, wherein the presence of intermediate filament protein fragments that have a C-terminal amino acid sequence in which the last three amino acid residues of said sequence are Ala Leu Asp in said sample is determined, wherein the determination is performed with an immunological assay using an antibody that has binding specificity to the amino acid sequence Glu Asp Phe Asn Leu Gly Asp Ala Leu Asp (SEQ ID NO: 1).

2. The method according to claim 1, wherein the biological sample is a sample of an organ, tissue or body fluid.

3. The method according to claim 2, wherein the body fluid is blood or serum.

4. The method according to claim 1, wherein the biological sample is from a human.

5. The method according to claim 1, wherein the rate of occurrence of cell apoptosis is determined.

6. The method according to claim 5, wherein the determined rate of cell apoptosis is used in the diagnosis of diseases with involvement of apoptosis.

7. The method according to claim 5, wherein the determined rate of cell apoptosis is used in the monitoring of an effect of therapy of diseases with involvement of apoptosis.

8. The method according to claim 6 or 7, wherein the diseases are degenerative diseases or cancer.

9. A method of determining the occurrence of cell apoptosis in a biological sample from a mammal, wherein the presence of intermediate filament protein fragments having a C-terminal amino acid sequence in which the last three amino acid residues of said sequence are Ala Leu Asp in said sample is determined, wherein the determination is performed with an immunological assay using an antibody that has binding specificity to the amino acid sequence Glu Asp Phe Asn Leu Gly Asp Ala Leu Asp (SEQ ID NO: 1) coupled to a carrier and/or label.

10. The method according to claim 9, wherein the biological sample is a sample of an organ, tissue or body fluid.

11. The method according to claim 9, wherein the body fluid is blood or serum.

12. The method according to claim 9, wherein the biological sample is from a human.

* * * * *